(12) United States Patent
Garigapati

(10) Patent No.: US 9,452,240 B2
(45) Date of Patent: Sep. 27, 2016

(54) PEPSINIZED COLLAGEN IMPLANTS AND BIOMEDICAL USES THEREOF

(71) Applicant: Orthovita, Inc., Malvern, PA (US)

(72) Inventor: Venkat R. Garigapati, Southborough, MA (US)

(73) Assignee: Orthovita, Inc., Malvern, PA (US)

( * ) Notice: Subject to any disclaimer, the term of this patent is extended or adjusted under 35 U.S.C. 154(b) by 128 days.

(21) Appl. No.: 14/209,320

(22) Filed: Mar. 13, 2014

(65) Prior Publication Data

US 2014/0277577 A1    Sep. 18, 2014

Related U.S. Application Data

(60) Provisional application No. 61/789,997, filed on Mar. 15, 2013.

(51) Int. Cl.
*A61L 27/24* (2006.01)
*A61L 27/56* (2006.01)
*A61L 27/54* (2006.01)

(52) U.S. Cl.
CPC ............... *A61L 27/56* (2013.01); *A61L 27/24* (2013.01); *A61L 27/54* (2013.01)

(58) Field of Classification Search
None
See application file for complete search history.

(56) References Cited

U.S. PATENT DOCUMENTS

| | | | |
|---|---|---|---|
| 4,294,241 A * | 10/1981 | Miyata | A61L 15/325 128/DIG. 8 |
| 4,505,855 A | 3/1985 | Bruns et al. | |
| 4,689,399 A | 8/1987 | Chu | |
| 5,028,695 A | 7/1991 | Eckmayer et al. | |
| 5,614,587 A * | 3/1997 | Rhee | A61K 47/48215 525/54.1 |
| 5,631,243 A | 5/1997 | Kelman et al. | |
| 5,750,146 A | 5/1998 | Jones et al. | |
| 5,874,537 A | 2/1999 | Kelman et al. | |
| 6,090,996 A | 7/2000 | Li | |
| 6,096,309 A | 8/2000 | Prior et al. | |
| 6,280,727 B1 | 8/2001 | Prior et al. | |
| 6,599,524 B2 | 7/2003 | Li et al. | |
| 6,716,225 B2 | 4/2004 | Li et al. | |
| 6,752,834 B2 | 6/2004 | Geistlich et al. | |
| 7,374,777 B2 | 5/2008 | Li et al. | |
| 7,807,192 B2 | 10/2010 | Li et al. | |
| 7,998,499 B2 | 8/2011 | Li et al. | |

FOREIGN PATENT DOCUMENTS

EP        0246013 A2    11/1987

OTHER PUBLICATIONS

Gekko et al, Increased Thermal Stability of Collagen in the Presence of Sugars and Polyols, J Biochem, 1983, vol. 94, pp. 199-205.*
Hirshburg et al, Collagen solubility correlates with skin optical clearing, Journal of Biomedical Optics, Jul./Aug. 2006 vol. 11, No. 4, pp. 040501-1-040501-3.*
Kuznetsova et al, Sugars and Polyols Inhibit Fibrillogenesis of Type I Collagen by Disrupting Hydrogen-Bonded Water Bridges between the Helices, Biochemistry 1998, vol. 37, pp. 11888-11895.*
"CollaGUARD Adhesion Barrier", Resorable Collagen Adhesion Barrier, <http://innocolline.com/collaguard-adhesion-barrier.html>, 2 pages.
Brigham et al., Tissue Engineering Part A, vol. 15, No. 00, pp. 1-9, 2009.
Cheng et al., Biomaterials 29, pp. 3278-3288, 2008.
McPherson, et al.,"Collagen Fibrillogenesis In Vitro: A Characterization of Fibril Quality as a Function of Assembly Conditions", Collagen Rel. Res. 5:119-135 (1985).
Shu-Tung Li, Biologic Biomaterials: Tissue-Derived Biomaterials (Collagen). In: Biomedical Engineering Handbook, Ed. J. D. Bronzino, 42-1 to 42-23, CRC Press, Inc. Boca Raton, Fla., 2000.
Silver et al., Journal of Biomaterials, 36, pp. 1529-1553, 2003.
Tanaka et al., Biomaterials 32, pp. 3358-3366, 2011.

* cited by examiner

*Primary Examiner* — Allison Fox
(74) *Attorney, Agent, or Firm* — Lerner, David, Littenberg, Krumholz & Mentlik, LLP

(57) ABSTRACT

Disclosed are pepsinized collagen implants, such as membranes and sponges, and methods of making them, which entails solubilizing pepsinized collagen in a buffer containing a polyol, e.g., mannitol or sorbitol, wherein the buffer has a substantially neutral pH. Methods of using the pepsinized collagen implants for clinical applications are also disclosed.

18 Claims, 2 Drawing Sheets

PEPSINIZED COLLAGEN IMPLANTS AND BIOMEDICAL USES THEREOF

CROSS-REFERENCE TO RELATED APPLICATION

The present application claims the benefit of the filing date of U.S. Provisional Patent Application No. 61/789,997, filed Mar. 15, 2013, the disclosure of which is hereby incorporated herein by reference.

BACKGROUND OF THE INVENTION

Collagen is the most abundant protein in the extracellular matrix of human tissue and plays important roles in providing structural support as well as performing other functions in tissue growth and regeneration. Apart from collagen, other types of extracellular matrix components such as proteoglycans, elastin, etc. also play important roles in maintaining tissue structure and function. Producing scaffolds simulating natural tissue is an essential enabling technology in the tissue engineering industry.

Collagen is an excellent natural biomaterial for tissue engineering because of its close resemblance to nature, low immunogenicity and excellent biocompatibility. However, unprocessed collagen usually has insufficient mechanical properties for it to be useful in engineering tissues in particular the weight-bearing tissues such as tendons, ligaments, intervertebral discs, etc. Unprocessed collagen is also difficult to manipulate and put sutures through during the implantation process. Further, unprocessed collagen is highly water swellable and is vulnerable to enzymatic digestion and thermal denaturation.

Known methods of making collagen membranes often involve extensive extraction procedures and lengthy isolation steps to obtain specific forms of collagen. These procedures often involve coacervation of collagen fibers, defatting, multi-cycle vitrification, extensive ultracentrifugation, and electrochemical plating, which are time consuming, difficult to scale up, and expensive. Tanaka, et al., Biomaterials 32:3358-66 (2011) reports on the production of transparent collagen laminates prepared by oriented flow casting, multi-cyclic vitrification, and chemical cross-linking of atelocollagen, which as known in the art is pepsin-solubilized Type I collagen. In addition to the aforementioned disadvantages associated with multi-cyclic vitrification, proteolytic digestion of collagen with enzymes such as pepsin requires strongly acidic conditions. Aside from the insolubility of pepsinized collagen in water, the acidic conditions present difficulties from the standpoint of preparing collagen implants that contain other bioactive materials.

Accordingly, there is a need in the art for methods of preparing collagen implants that do not suffer from one or more of the aforementioned disadvantages.

BRIEF SUMMARY OF THE INVENTION

A first aspect of the present invention is directed to a method of preparing a collagen implant for use in tissue repair, that entails (a) digesting collagen with pepsin, thus producing pepsinized collagen; (b) solubilizing the pepsinized collagen in a buffer composition having a substantially neutral pH, and which comprises a polyol; (c) drying the thus-solubilized, pepsinized collagen, forming the pepsinized collagen implant; and optionally (d) reacting the implant with a cross-linking agent. The implants may be produced in the forms of membranes and sponges.

A second aspect of the present invention is directed to a collagen implant made by the inventive process. The membranes may be formulated to be transparent or semi-transparent, and shaped and sized for purposes of specific clinical applications, e.g., implants in the form of grafts or prosthetics. In some embodiments, the implant may be imparted with anti-adhesive properties. In these embodiments, the pepsinized collagen is formulated in the buffer composition that further includes an anti-adhesive agent, e.g., a sugar, a PEGylated amine, a PEGylated carboxylic acid, a short chain aliphatic acid anhydride or fatty acid anhydride, or a positively charged amino acid, or a copolymer or homopolymer thereof.

Yet other aspects of the present invention are directed to methods of using the collagen implants. The pepsinized collagen sponges can be used in clinical applications such as hemostasis and wound repair. The pepsinized collagen membranes can be used in clinical applications such as tissue repair or generation, or for promoting or facilitating tissue grafts, that entail covering an area of damaged, injured, diseased, wounded, removed, or missing tissue of a body of a subject.

The methods of the present invention are advantageous in several respects, particularly with respect to implants based on Type I collagen. Type I collagen exists in fibril form that is not soluble in aqueous media at pH 5 to 7.4. It is soluble in acidic media only at very low concentrations. Applicant has surprisingly and unexpectedly discovered that the inclusion of a polyol in a buffer solution having a substantially neutral pH solubilizes the pepsinized collagen readily quickly and substantially completely, such that it undergoes self-assembly. Upon drying, the solution forms membranes or sponges.

There are several Type I collagen-based membranes which are not ideal for repair as they often result in capsule formation and or mineralization as they are fully developed collagen fibrils. In addition, they have been known to be immunogenic. The pepsinized collagen membranes of the present invention are relatively advantageous in these respects. The pepsinized collagen undergoes reassembly internally following implantation in the body so that the immunogenicity is far less compared to the stand alone Type I-based collagen products. Moreover, integration of the present membranes with the host tissue is expected to be improved. Toughness and elasticity of these products may also be easily varied to accommodate a variety of clinical uses.

Even further, the pH range of the buffer does not adversely affect or detract from the beneficial medicinal properties and uses of the collagen implant. It also facilitates addition of other biomaterials into the buffer, for purposes of incorporating them into the collagen implant.

In some embodiments, the collagen implants are transparent or semi-transparent, which provides an advantage of allowing for the direct and non-invasive monitoring of the healing process such as a wound visually through the membrane.

DETAILED DESCRIPTION

Figure 1:
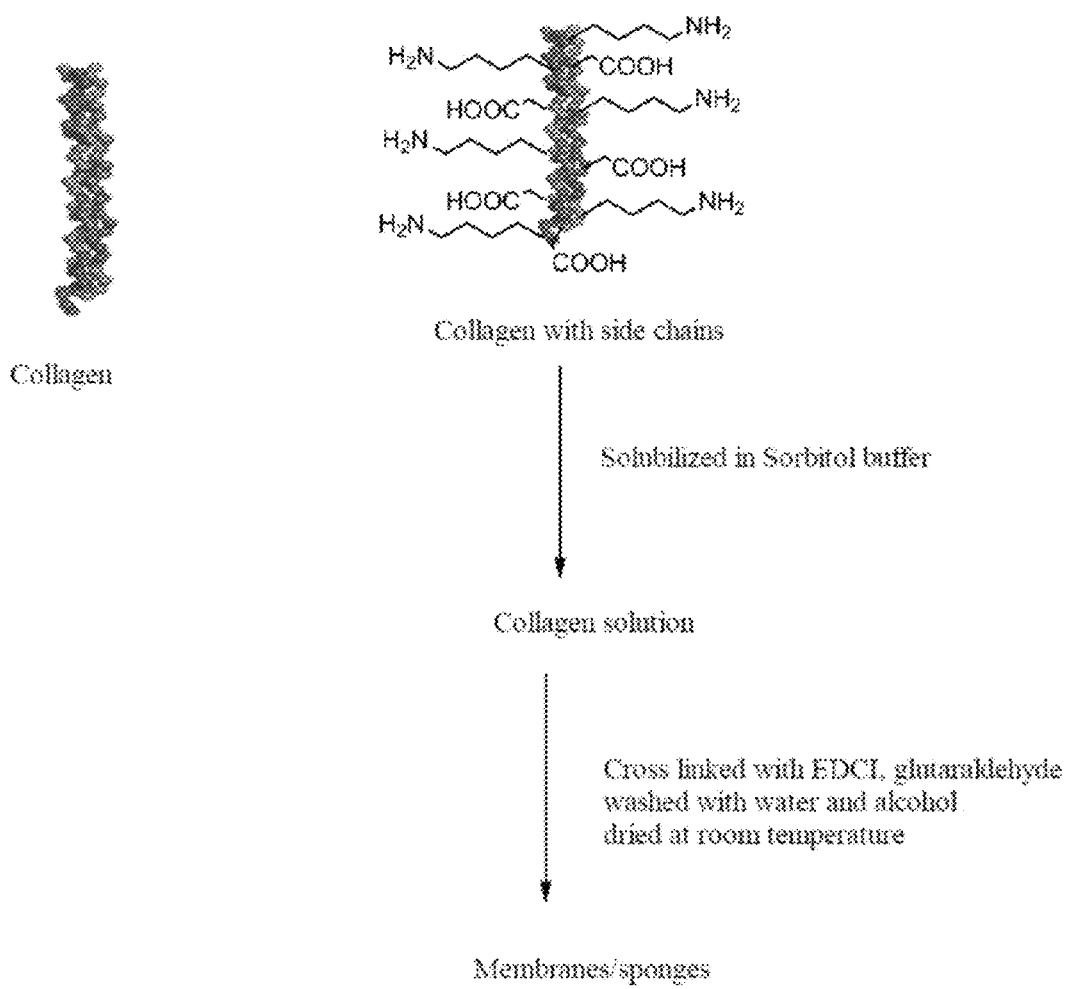
FIG. 1 is a schematic illustration of an embodiment of the method of the present invention.
Figure 2:
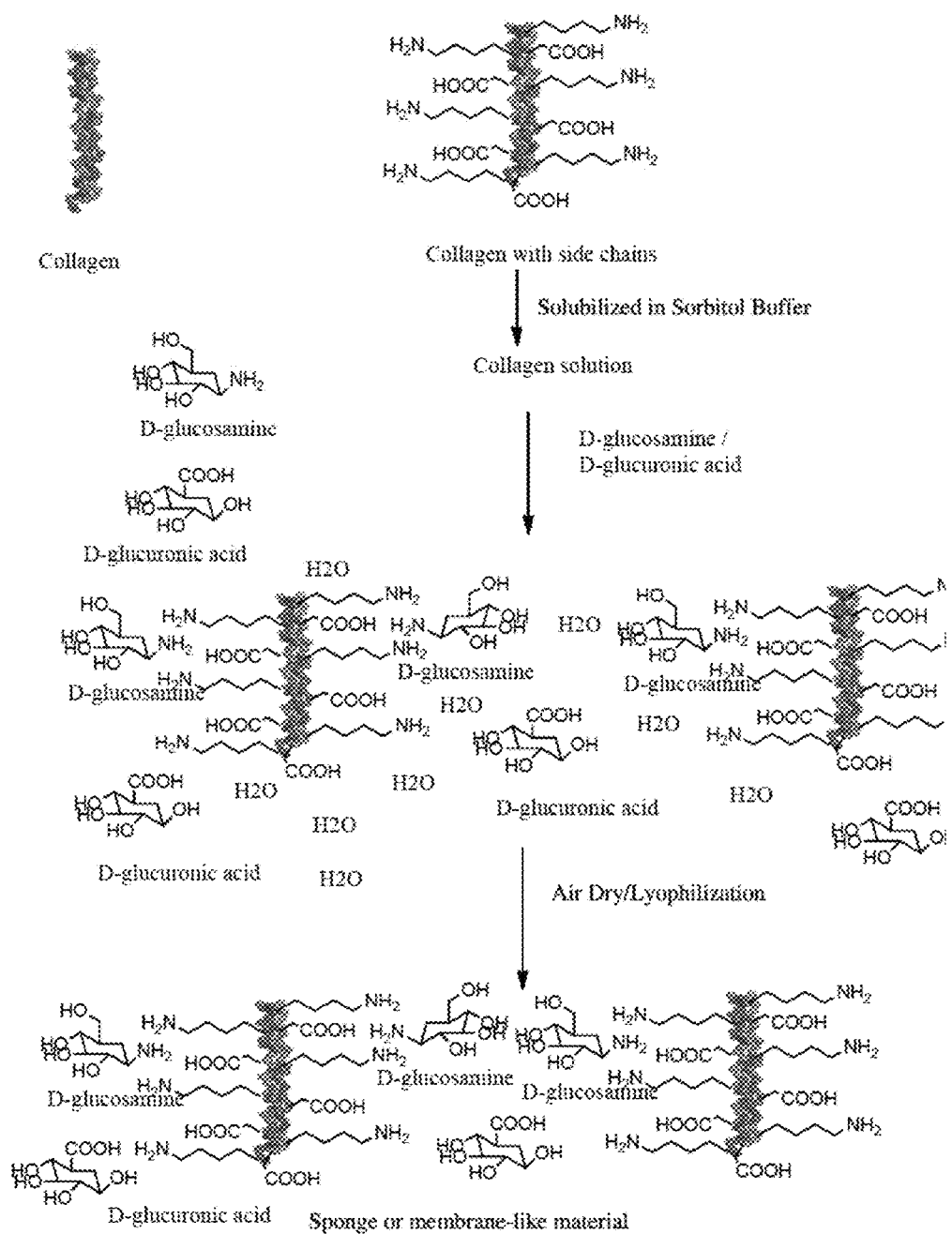
FIG. 2 is a schematic illustration of an embodiment of the method of the present invention wherein the collagen implant has pendant glucuronic acid and glucosamine residues.

Collagen for use in the present invention may be obtained from a variety of sources including, for example, bovine hide. Pepsinization of collagen may be performed in accordance with standard procedures. See, e.g., McPherson, et al., Collagen Rel. Res. 5:119-135 (1985) (describing pepsin solubilization of collagen using bovine corium). In some embodiments, bovine hides such as male bovine hides derived from a controlled herd may be cold shipped with a maximum time allowed between slaughter and trimming, and then soaked in acetic acid in order to minimize degradation and to reduce bioburden. The soaked and trimmed hides may then be ground up and digested in a temperature and pH-controlled vessel using a pepsin citrate solution as the primary digestive agent. A settling step may then be conducted, using diatomaceous earth to filter out extraneous cellular material, followed by a viral inactivation step e.g., using NaOH, to inactivate prions. The pepsinized collagen may be further purified using known techniques, e.g., ultra-filtration at a pH of about 2.0.

The amount of pepsinized collagen that is added to the buffer generally ranges from about 0.1 mg to about 60 mg, and in some embodiments from about 1 to about 30 mg, and in yet other embodiments from about 2 to about 20 mg, per 1 ml of buffer.

Buffers that may be useful in the present invention are known in the art. Representative examples of buffers include physiologically acceptable buffers such as saline, phosphate buffered saline, etc., and which may include salts such as sodium acetate, calcium acetate, sodium succinate dibasic, and calcium propionate. The buffer is chosen or formulated so as to have a substantially neutral pH, which for purposes of the present invention, refers to a pH at which the pepsinized collagen is readily solubilized (e.g., in a matter of minutes at room temperature). The pH generally ranges from about 5 to about 8, and in some embodiments from about 5.5 to about 7.5, and in yet other embodiments from about 6 to about 7.5, and in yet other embodiments from about 6 to about 7. The amount of buffer varies, depending on factors such as the amount of pepsinized collagen. Agents for adjusting the pH, e.g., HCl, may be used to achieve the desired pH. Other inert excipients known to those in the art may also be added.

The buffer solution contains a polyol. Useful polyols in the present invention include $C_4$-$C_6$ polyols, representative examples of which include sorbitol, mannitol, and xylitol. The amount of the polyol generally ranges from about 1 to about 30 grams per 100 ml of buffer, and in some embodiments from about 2.5 to about 20 grams per 100 ml of buffer, and in yet other embodiments from about 5 to about 10 grams per 100 ml of buffer (i.e., from about 5% to about 10% (w/v)).

A variety of other ingredients may be added to the buffer prior to the drying step in order to be incorporated into the collagen implant. Such ingredients may be added to optimize one or more physical properties of the collagen membrane, as well as to provide certain medicinal or therapeutic benefits depending upon the ultimate clinical application. In some embodiments, other types of collagen may be added such as non-pepsinized collagen fibers, Type I collagen, Type II collagen, and Type III collagen and Type IV collagen. For example, depending on the desired physical properties (e.g., sponginess, elasticity, toughness), Type I collagen may be present. Type I collagens include native fibrous insoluble human, bovine, porcine, or synthetic collagen, soluble collagen, reconstituted collagen, and microfibrillar forms of collagen as described, for example, in U.S. Pat. Nos. 6,096,309 and 6,280,727. The weight ratio of the Type I collagen to the pepsinized collagen generally varies from about 0.01 to about 0.99, and in some embodiments from about 0.1 to about 0.9, and yet in other embodiments from about 0.2 to about 0.5.

Yet other types of additional ingredients, such as therapeutically active or beneficial agents may be added and become incorporated into the pepsinized collagen implants. Representative examples of such agents include antibiotics, analgesics, anti-inflammatory agents, cells, growth factors and other non-cellular agents. Active agents may be added to the buffer composition before drying; they may be added after drying and before packaging; or (e.g., in the case of sponges) they may be added suitably prior to the clinical application or procedure.

Representative examples of antibiotics include tetracyclines such as tetracycline, doxycycline and aureomycin; penicillins including penicillin V, ampicillin, amoxicillin, bacampicillin, cabenicillin, carbenicillin, cloxacillin, dicloxacillin, nafcillin and oxacillin; cephalosprins such as cephalexin, cephradine, cefadroxil, cefaclor, cefuroxime axetil, cepfodoxime, loracarbef and cefixime; aminoglycosides such as gentamycin sulfate, tobramycin, amikacin, netimicin and neomycin; polymicins such as polymixin B; and sulfonamides such as mafenide, silver sulfadiazine and sulfasalazine.

Representative examples of analgesics include morphine, narcotic antagonists (e.g., naloxone), local anesthetics (e.g., lidocaine, bupivacaine, mepivacaine, dibucaine, prilocaine, etidocaine, ropivacaine, procaine, tetracaine, etc.), glutamate receptor antagonists, adrenoreceptor agonists, adenosine, canabinoids, cholinergic and GABA receptors agonists, and neuropeptides.

Representative examples of anti-inflammatory agents include anti-cytokine agents such as TNF-α inhibitors, IL-1 inhibitors, IL-6 inhibitors, IL-8 inhibitors, IL-12 inhibitors, IL-15 inhibitors, IL-10, NF-κβ inhibitors, and interferon-gamma (IFN-gamma).

The compositions may further include cells. Cells may be autologous, allogenic, xenogenic, or a combination thereof. Suitable types of cells include, for example, stem cells, mesenchymal stem cells, and/or progenitor cells, including cells derived from bone marrow, synovial fluid, synovium, placenta, umbilical cord, skin, muscle, and fat/adipose tissue, Schwann cells, endothelial cells, epithelial cells, Sertoli's cells, fibroblasts, or any cells useful or desirable in applications for tissue repair or regeneration. Cells may also be differentiated cells including, for example, chondrocytes, tenocytes, osteoblasts, and synoviocytes. The composition may include one type of cells or a combination of two or more cell types.

The compositions may further include other, non-cellular therapeutically beneficial agents such as growth factors (e.g., TGF-β, EGF, FGF, IGF-1 BMP-7 and OP-1, etc.), glycosaminoglycans (GAGs) (e.g., aggrecan, decorin, biglycan and fibromodulin), chemokines and cytokines (e.g., interleukins and interferons), chitosan and hyaluronan. Extracellular matrix molecules that bind to growth factors, e.g., heparan sulfate and proteoglycans, may advantageously be added to serve as a reservoir for the factors.

In some embodiments, the collagen implant may be prepared so as to possess anti-adhesive properties, which in the context of the present invention, refers to substantially reduced adhesion to neighboring tissues and organs. To impart the anti-adhesive property, the buffer composition may be formulated so as to further include an anti-adhesive agent. Examples of such agents include saccharides, e.g., monosaccharides such as mannose, fucose, glucose, galactose, glucuronic acid, glucosamine, and N-acetyl glucosamine. Glucuronic acid and N-acetyl glucosamine are the monomeric building blocks of hyaluronic acid. The saccharide may be added to the buffer in the form of a physiologically acceptable salt, e.g., a hydrochloride salt. Other examples of anti-adhesive agents that may be suitable for use in the present invention include anhydrides of short-chain aliphatic dicarboxylic acids such as maleic acid, succinic acid, and itaconic acid, as well as fatty acid anhydrides (e.g., anhydrides of saturated or unsaturated $C_{12}$-$C_{18}$ fatty acids).

Further examples of anti-adhesive agents that may be suitable for use in the present invention include positively charged amino acids, e.g., lysine, arginine, histidine and glutamic acid, and copolymers and homopolymers thereof, e.g., polyarginine, polylysine, polyglutamic acid, and polyhistidine.

Further examples of anti-adhesive agents that may be suitable for use in the present invention include polyethylene glycols derivatized with amine or carboxylic acid groups. Representative examples of PEGylated amines may be represented by the formula

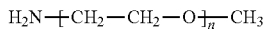

wherein n is an integer from 4 to 24, e.g., 4, 8, 12, or 24. Other examples of PEGylated amines may be represented by the formula:

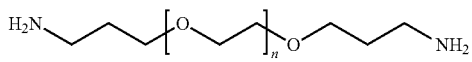

wherein n is such that the average molecular weight (Mn) of the PEGylated carboxylic acid is about 1500.

Representative examples of PEGylated carboxylic acids that may be suitable for use in the present invention may be represented by the formula:

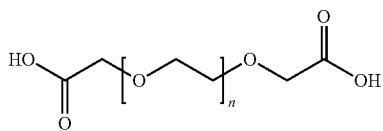

wherein n is such that the average molecular weight (Mn) of the PEGylated carboxylic acid is about 600. Other examples of PEGylated carboxylic acids may be represented by the formula below:

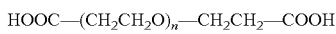

wherein n is an integer of from 4 to 24, e.g., 4, 8, 12 or 24.

The amount of the anti-adhesive agent present in the buffer composition may vary, e.g., depending on the desired degree of transparency. In general, the amount of this agent present in the buffer composition is from about 0.1 mg/ml to about 200 mg/ml, and in some embodiments, from about 0.5 mg/ml to about 50 mg/ml (w/v).

The degree of transparency may be achieved by adjusting the thickness of the membrane (which is influenced by the amount of the concentration of the pepsinized collagen in the buffer), the pH of the buffer, and the presence of various additives such as the polyol and the salt(s) in the buffer. The term "transparent" means that the composition is sufficiently clear in the visible light range as to result in an absorbance of less than 0.6 OD units when measured with light having a wavelength at 410 nm through a 1 millimeter sample of the composition.

Following addition of the desired materials, the solution, which due to the presence of the pepsinized collagen, is viscous in nature, is dried. Drying may be conducted in accordance with standard techniques such as air drying (at normal pressure or under vacuum) and lyophilization. In some embodiments, sponges may be obtained through lyophilization. In some embodiments, transparent and semi-transparent membranes may be obtained by air drying. The amount of time for drying will vary, e.g., depending upon whether the solution is subjected to heat.

Following drying, the resultant collagen implant may be subjected to cross-linking for purposes of structural integrity. This step may be conducted in accordance with standard procedures and reagents in the art, e.g., 1-Ethyl-3-[3-dimethylaminopropyl]carbodiimide hydrochloride (EDC), glutaraldehyde (in liquid or vapor form), and genipin. The amount of cross-linking agent may vary, e.g., depending upon the desired elastic properties and toughness, and in general ranges from about 0.01 to about 30%, and in some embodiments from about 0.05 to about 20%, and in yet other embodiments to about 0.01 to about 6% (w/v).

The implant may then be further formed or shaped (with appropriate dimensions) for the intended clinical purpose, as known in the art. In some embodiments, the pepsinized collagen membrane may be included in a multi-layer structure that contains a backing layer, for example, which serves to shield the collagen membrane from the in-growth of native tissue cells from one side. See, e.g., Shu-Tung Li, Biologic Biomaterials: Tissue-Derived Biomaterials (Collagen). In: Biomedical Engineering Handbook, Ed. J. D. Bronzino, 42-1 to 42-23, CRC Press, Inc. Boca Raton, Fla., 2000. The implants may be sterilized by methods known in the art, e.g., gamma irradiation, e-beam, ethylene oxide (EtO), steam and dry heat, and packaged (or vice versa). The packages may contain in a separate container (e.g., a vial) a therapeutically active or beneficial agent so it can be added to (e.g., disposed on) the implant just prior to implantation.

The resulting implants may be employed in a variety of clinical applications known in the art. See, e.g., U.S. Pat. No. 6,716,225 (nerve repair); U.S. Pat. No. 7,807,192 (repair of pericardium tissue after open-heart surgery, repair of hernia of the abdominal-wall); U.S. Pat. No. 7,374,777 (repairing meningeal tissue); U.S. Pat. No. 6,752,834 (reconstruction of bone or cartilage tissue). The collagen sponges, for example, may be useful in hemostasis and wound closure. The collagen membranes may be useful in soft tissue repair constructions that ordinarily utilize artificial membranes, such as skin grafting procedures (e.g., burned skin replacements), tendon reconstruction, and wound repair. They may also be shaped into various forms and used in connection with hard tissue repair. The membranes may be used in their two-dimensional configuration by successively packing the membranes into a defect, such as a cranial or periodontal cavity. The membranes may be reformed into three dimensional objects for implantation in replacing sections of bone by rolling into cylinders, or by stacking and cutting to shape.

Pepsinized collagen implants that have anti-adhesive properties may be particularly advantageous in various clinical applications, e.g., as an anti-adhesion barrier for separating various tissue and organs, or as a surgical guide that is place in vivo at a site in which multiple surgical procedures are to be performed over a period of time. For instance, in certain spinal procedures, the collagen membranes of the present invention may be folded and placed in vivo over the spine after a procedure, such as a laminectomy, is performed, and which needs to be re-accessed. In this instance, the folded membrane is placed such that it extends from a perpendicular plane of the surgical site up to the surface of the skin. In the subsequent surgery at a later time, the edges of the membrane can be followed for direct access to the surgical site providing the surgeon with an unblocked path to the spine.

Yet other clinical applications that may exploit the properties of the anti-adhesive implants include gynecological procedures, abdominal surgical procedures, inguinal or femoral hernia repair, and in the treatment of large burns. For example, in the course of gynecological and abdominal surgical procedures, the membrane can be applied directly to the organ that is operated upon, and which separates the organ from the surrounding tissue, as it slowly dissolves over the course of time, e.g., which in some embodiments is from about 2 to about 12 weeks, during which time the organ or tissue is allowed to heal without adhesion to the surrounding tissue.

The invention is now described in terms of the following non-limiting examples. Example 1 describes the preparation of a buffer. Example 2 describes preparation of a pepsinized collagen sponge. Examples 3-14 describe preparation of pepsinized collagen membranes.

EXAMPLE 1

Sodium acetate (4.1 g), calcium propionate (5.906 g) and sorbitol (50 g) were dissolved in 400 ml of deionized water in volumetric flask. The volume was adjusted to 500 ml mark by adding additional water. The pH of the solution was adjusted to 7.4 by 0.01 N HCl solution. This is referred to hereinafter as the "sorbitol buffer."

EXAMPLE 2

Wet pepsinized collagen (10 g) was mixed with sorbitol buffer (40 ml) at pH 7.4. The viscous soluble solution was poured into a tray and lyophilized. The resultant sponge was cross-linked by EDCI in alcohol (100 ml) and triethylamine (100 microliters) at room temperature for 6 hours. The sponge was washed with water and alcohol and dried at room temperature under vacuum. The resultant sponge was highly porous, flexible, and had a full or fluffy appearance.

EXAMPLE 3

Wet pepsinized collagen (10 g) was solubilized in sorbitol buffer (40 ml) at pH 7.4. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes. This was dried at room temperature under vacuum.

EXAMPLE 4

Wet pepsinized collagen (10 g) was mixed with sorbitol buffer (2 ml) at pH 7.4. The viscous semi-soluble solution was poured into a tray and lyophilized. The resultant membrane was cross-linked by EDCI in alcohol (100 ml) and triethylamine (100 microliters) at room temperature for 6 hours. The membrane was washed with water and alcohol to give a semi-transparent membrane. This was dried at room temperature under vacuum. The membrane was smooth and thin in appearance.

EXAMPLE 5

Wet pepsinized collagen (10 g) was solubilized in sorbitol buffer (40 ml) at pH 7.4. To this, 800 mg of D-glucosamine HCl was added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 6

Wet pepsinized collagen (10 g) was solubilized in sorbitol buffer (40 ml) at pH 7.4. To this, 800 mg of D-glucosamine HCl was added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 7

Wet pepsinized collagen (10 g) was solubilized in sorbitol buffer (40 ml) at pH 7.4. To this, 600 mg of poly (ethyleneglycol) bis (carboxymethyl) ether, Mn 600, was added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 8

Wet pepsinized collagen (10 g) was solubilized in sorbitol buffer (40 ml) at pH 7.4. To this 1 g of poly (ethyleneglycol) bis-(3-aminopropyl) terminated, Mn 1500, was added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 9

Wet pepsinized collagen (10 g) was solubilized in sorbitol buffer (40 ml) at pH 7.4. To this, 1 g of D-glucuronic acid was added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 10

Wet pepsinized collagen (10 g) was solubilized in sorbitol buffer (40 ml) at pH 7.4. To this, 0.4 g of D-glucuronic acid and 0.4 g of D-glucosamine were added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 11

Wet pepsinized collagen (10 g) was solubilized in sorbitol buffer (40 ml) at pH 7.4. To this 0.2 g of D-glucuronic acid, 0.2 g of D-glucosamine and 0.1 g of L-lysine were added and mixed to dissolve it. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 12

Wet pepsinized collagen (10 g) was solubilized in sorbitol buffer (40 ml) at pH 7.4. To this, 0.25 g of succinic anhydride was added followed by 200 microliters of triethylamine. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 13

Wet pepsinized collagen (10 g) was solubilized in sorbitol buffer (40 ml) at pH 7.4. To this, 50 mg of PEG-amine (8 arm, mol wt 20 K) was added and the mixture was vortexed to dissolve. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

EXAMPLE 14

Wet pepsinized collagen (10 g) was solubilized in sorbitol buffer (40 ml) at pH 7.4. To this, 150 mg of polyglutamic acid was added and the mixture was vortexed to dissolve. The viscous transparent solution was poured into a tray and air dried at room temperature. The resultant membranes were cross-linked by EDCI in alcohol (100 ml) and triethylamine (100 microliters) at room temperature for 6 hours. The membranes were washed with water and alcohol to give transparent membranes having anti-adhesive properties. This was dried at room temperature under vacuum.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a collagen implant for use in tissue repair, comprising:
   (a) digesting collagen with pepsin, thus producing pepsinized collagen;
   (b) solubilizing the pepsinized collagen in a buffer composition comprising a polyol, wherein the buffer has a substantially neutral pH;
   (c) drying the thus-solubilized, pepsinized collagen; and optionally
   (d) reacting the collagen of (c) with a cross-linking agent, thus producing the collagen implant.

2. The method of claim 1, wherein the collagen is present in the buffer composition in an amount of about 2 mg to about 20 mg per ml of the buffer.

3. The method of claim 1, wherein the pH of the buffer composition is from about 6 to about 7.5.

4. The method of claim 1, wherein the polyol is present in the buffer composition in a concentration of about 5% to about 10% (w/v).

5. The method of claim 1, wherein the polyol is sorbitol.

6. The method of claim 1, wherein the polyol is mannitol.

7. The method of claim 1, further comprising adding Type-I collagen fibers to the buffer composition prior to drying.

8. The method of claim 7, wherein the Type-I collagen fibers and the pepsinized collagen are present in the buffer composition in a weight ratio of about 1:5 to about 1:2.

9. The method of claim 1, further comprising adding an anti-adhesive agent to the buffer composition prior to the drying.

10. The method of claim 9, wherein the anti-adhesive agent includes glucuronic acid, glucosamine, or a combination thereof.

11. The method of claim 9, wherein the anti-adhesive agent includes succinic anhydride.

12. The method of claim 9, wherein the anti-adhesive agent includes bis(3-aminopropyl)polyethylene glycol having an average molecular weight (Mn) of about 1500.

13. The method of claim 9, wherein the anti-adhesive agent includes poly(ethylene glycol)bis(carboxymethyl)ether having a Mn of about 600.

14. The method of claim 9, further comprising adding to the buffer composition, or to the formed implant, at least one therapeutically active or beneficial agent selected from the group consisting of antibiotics, analgesics, anti-inflammatory agents, cells, growth factors, and combinations of two or more thereof.

15. The method of claim 1, wherein the drying comprises lyophilization.

16. The method of claim 9, wherein the drying comprises air drying.

17. The method of claim 1, wherein the cross-linking agent comprises 1-Ethyl-3-[3-dimethylaminopropyl]carbodiimide hydrochloride (EDC), glutaraldehyde, or genipin.

18. The method of claim 17, wherein the cross-linking agent is added to the solubilized, pepsinized collagen in a concentration of about 0.1% to about 6% (w/v).

* * * * *